United States Patent [19]
Guettler et al.

[11] Patent Number: 5,521,075
[45] Date of Patent: May 28, 1996

[54] METHOD FOR MAKING SUCCINIC ACID, ANAEROBIOSPIRILLUM SUCCINICIPRODUCENS VARIANTS FOR USE IN PROCESS AND METHODS FOR OBTAINING VARIANTS

[75] Inventors: Michael V. Guettler, Holt; Mahendra K. Jain, Okemos, both of Mich.

[73] Assignee: Michigan Biotechnology Institute, Landsing, Mich.

[21] Appl. No.: 359,152

[22] Filed: Dec. 19, 1994

[51] Int. Cl.$^6$ ................... C12P 7/46; C12P 1/04
[52] U.S. Cl. ............ 435/145; 435/252.1; 435/822
[58] Field of Search ................ 435/145, 252.1, 435/172.1, 244, 822

[56] References Cited

U.S. PATENT DOCUMENTS

| | | | |
|---|---|---|---|
| 5,143,833 | 9/1992 | Datta | 435/145 |
| 5,143,834 | 9/1992 | Glassner et al. | 435/145 |
| 5,168,055 | 12/1992 | Datta et al. | 435/145 |

OTHER PUBLICATIONS

Podkovyrov SM et al, J. Gen. Microbiol. 139(2):223–228 (1993).
Samuelov NS et al, App Environ Microbiol 57(10):3013–3019 (1991).
Rothstein, D. M., (1986). *Clostridium thermosaccharolyticum* strain deficient in acetate production. J. Bacteriol. 165:319–320.

*Primary Examiner*—Michael G. Wityshyn
*Assistant Examiner*—S. Saucier
*Attorney, Agent, or Firm*—Quarles & Brady

[57] ABSTRACT

A method for making succinic acid employs a fluoroacetate resistant variant of *Anaerobiospirillum succiniciproducens*. The fluoroacetate variant produces a succinic acid product which contains less acetic acid than the product obtained using the parent strain under identical conditions. A preferred variant FA-10 is obtained from *A. succiniciproducens* (ATCC No. 29305). A method of obtaining the variant also is described.

5 Claims, No Drawings

METHOD FOR MAKING SUCCINIC ACID, ANAEROBIOSPIRILLUM SUCCINICIPRODUCENS VARIANTS FOR USE IN PROCESS AND METHODS FOR OBTAINING VARIANTS

FIELD OF THE INVENTION

This invention relates to a method for making succinic acid, variants of succinic acid producing organisms that produce a product containing low concentrations of acetic acid, and methods for obtaining such variants.

BACKGROUND OF THE INVENTION

Succinic acid and its derivatives are widely used as specialty chemicals for applications in foods, pharmaceuticals, and cosmetics.

The Glassner et al. U.S. Pat. No. 5,143,834 and the Datta et al. U.S. Pat. No. 5,168,055, disclose integrated processes for the production of succinic acid. These patents employed the anaerobic bacterium *A. succiniciproducens* which produces major amounts of succinic and acetic acids in approximately a 4 to 1 ratio. The Glassner et al. patent discloses that after conventional electrodialysis, water-splitting electrodialysis, cation exchange, and anion exchange the resulting final product contains 19.9% acetate and 79.6% succinate on a dry weight basis.

The elimination of the acetate in the fermenter broth would vastly improve the final succinic acid product since acetate is the major impurity in an otherwise highly purified product. One method of eliminating acetate would be to use a microorganism that produces less or no acetate. Aside from an improved electrodialysis product there are other possible benefits in having a microorganism that produces less acetate. These include reduced toxicity from acetate and an increase in succinate yield. The accumulation of acetate contributes to the cessation of growth and fermentation by the producing organism, and the effect is particularly pronounced at a low external pH (1). In addition, since *A. succiniciproducens* produces succinic acid only at the low end of its pH range (6.0–6.2), the elimination of acetate accumulation could extend the biocatalytic life of the *A. succiniciproducens* biomass. Furthermore, because it is necessary in order to increase the succinate yield to increase the amount of carbon flow in the succinate specific pathway, additional carbon could be diverted to succinate by strains which produce less acetate.

It would be advantageous to have a method for making a product containing more succinic acid and containing less acetic acid. It also would be advantageous to have microorganisms for use in such a method and a method of obtaining such microorganisms.

BRIEF SUMMARY OF THE INVENTION

The objects of the present invention are to disclose a fermentation method for making a product containing more succinic acid and containing less acetic acid, microorganisms for use in such a method and a method of obtaining such microorganisms.

The method of the present invention for making succinic acid comprises providing an aqueous fermentation medium containing a culture of a microorganism and a source of fermentable carbon; cultivating said organism under anaerobic conditions in the presence of carbon dioxide to form succinic acid in a concentration of at least about 25 g/L in the fermentation medium.

The microorganism used in the above method is a variant of a parent strain of *A. succiniciproducens* which is more resistant to fluoroacetate than the parent and which produces less acetic acid in the fermentation method than a corresponding fermentation using the parent strain under otherwise identical conditions. These variants are obtained without the use of genome disruptive non-directed mutagens. We have discovered that such variants of *A. succiniciproducens* can be used in a method of making succinic acid to produce very small amounts of acetate so that the fermentation product has a succinic/acetic ratio of as high as 85. These variants permit the production of a superior succinic acid product because the acetate is the only major impurity that is not readily removed by electrodialysis.

The method of the present invention for obtaining variants of *Anaerobiospirillum succiniciproducens* which upon fermentation produces less acetate than the parent organism, comprises growing a parent strain of *Anaerobiospirillum succiniciproducens* upon plates of a nutrient medium containing fermentable carbon and about 1.0 g/l to about 15 g/l of sodium monofluoroacetate, under anaerobic conditions in a first container, transferring well isolated colonies of resistant *Anaerobiospirillum succiniciproducens* strains to second containers containing the same nutrient medium without fluoroacetate, incubating the second containers under similar conditions, measuring the amount of acetic acid produced by the *Anaerobiospirillum succiniciproducens* in the second containers, and thereby isolating in the second containers the colonies of the *Anaerobiospirillum succiniciproducens* variants which produce low amounts of acetic acid, and then growing and isolating colonies of the desired variants which produce high concentrations of succinic acid and low concentrations of acetic acid.

DESCRIPTION OF THE PREFERRED EMBODIMENT OF THE INVENTION

In the preferred practice of the present invention, a substantially pure culture of the variant FA-10 of *A. succiniciproducens* (ATCC 55617) which was deposited in the American Type Culture Collection, 12301 Parklawn Drive, Rockville, Md. 20852 on Sep. 29, 1994 is anaerobically grown at a controlled pH between about 6.0 to about 6.5 in a fermenter on a medium containing a source of fermentable carbon containing a carbohydrate and other nutrients, such as corn steep liquor; tryptophan; and, sodium ions under a partial pressure of at least about 0.1 atmosphere $CO_2$ until the fermentation broth contains at least about 25 g/l of succinate.

The source of assimilable carbon used in the practice of this invention can be any carbohydrate that is fermented by the strain of bacterium used. These carbohydrate sources include dextrose, sucrose, fructose, lactose, soluble starches, and corn syrups. The fermentation is conducted in an aqueous medium containing tryptophan, sodium ions and dissolved carbon dioxide. Other nutrients and growth factors needed for the growth and the reproduction of the microorganism employed also are added to the medium.

The concentration of carbohydrate in the medium is between about 20 g/l to about 55 g/l, preferably between about 30 g/l and about 50 g/l. Carbohydrate concentrations above about 60 g/l give solutions with such high osmotic pressures that the organisms do not grow well.

Carbon dioxide can be supplied to the fermentation medium in various ways. The medium can be sparged with $CO_2$ gas. The fermentation can be run in a pressurized reactor which contains carbon dioxide at superatmospheric pressure. The $CO_2$ can be mixed with other gases as long as the gases employed do not interfere with the growth and metabolism of the organism employed. Carbon dioxide can also be supplied to the fermentation medium by the addition of carbonates or bicarbonates which generate this gas under the conditions of the fermentation. The medium should contain dissolved $CO_2$ in equilibrium with a minimum of about 0.1 atmosphere partial pressure of carbon dioxide. In the preferred embodiment, the medium is saturated with carbon dioxide and the atmosphere contains about 0.3 atmosphere partial pressure of carbon dioxide or higher.

In order to obtain good production of succinate salt, the pH of the medium is maintained in the range of from about 6.0 to about 6.5. The pH is conveniently maintained by the addition of alkaline carbonates, alkaline earth hydroxides, or mixtures thereof.

The fermentation process of this invention is carried out at a temperature between about 30° C. and about 42° C. Optimum growth of the FA-10 variant of *A. succiniciproducens* organism is at about 39° C. Since this is a strict anaerobe, fermentations using the organism are carried out under anaerobic conditions in a medium which has been sterilized by heat or other means well known in the fermentation art.

In the preferred process the succinate salt-containing whole broth, preferably will contain about 25 to about 50 g/l succinic acid, and usually between about 0.1 to about 1.0 g/l of acetic acid.

The preferred microorganism FA-10 (ATCC No. 55617) is an isolated, biologically pure variant of *Anaerobiospirillum succiniciproducens* ATCC No. 29305.

The preferred variant FA-10 of *A. succiniciproducens* has been demonstrated to grow well on media containing carbohydrates, preferably dextrose; other nutrients, including corn steep liquor; sodium ions; and at least about 10 ppm tryptophan in the presence of a partial pressure of at least 0.1 atmosphere of $CO_2$ at a temperature of about 39° C. This strain is capable of producing high concentrations of succinate (about 25 to about 55 g/l) with a high productivity.

The variant FA-10 is obtained as previously described and as more specifically described in the description of the experimental work.

EXPERIMENTAL WORK

Materials and Methods
Organisms:

The acetate minus strain FA-10 (ATCC No. 55617) was derived from *Anaerobiospirillum succiniciproducens* ATCC 29305 in a Michigan Biotechnology Institute laboratory. The *Anaerobiospirillum succiniciproducens* ATCC 29305 was obtained from the American Type Culture Collection (ATCC), Rockville, Md.
Media:

All media was prepared anaerobically. Phosphate buffered basal (PBB) medium was prepared so that one liter contained the following: $NH_4Cl$ 1.5 g; NaCl 1.35 g; $MgCl_2$-$6H_2O$ 0.3 g; $CaCl_2 \cdot 2H_2O$ 0.15 g; nitrilotriacetic acid 0.13 g; resazurin 3 mg; $CoCl_2$-$6H_2O$ 1.7 mg; $FeSO_4$-$7H_2O$, $MnCl_2$ $4H_2O$, $CaCl_2$ $2H_2O$, $ZnCl_2$ 1.0 mg; $Na_2SeO_3$ 0.17 mg; $CuCl_2$ $2H_2O$ 0.2 mg; $NiSO_4$-$6H_2O$ 0.26 mg; $Na_2MoO_4$, $H_3BO_3$ 0.1 mg. One liter of *Anaerobiospirillum succiniciproducens* (ANS) defined medium was PBB supplemented as follows: glucose 20 g; $KH_2PO_4$ 6.0 g; $K_2HPO_4$ 11.6 g; cysteine 500 mg; tryptophan 25 mg; methionine 50 mg; $B_{12}$ 1 µg; biotin, folic acid 20 mg; thiamine, riboflavin, niacin, pantothenate, p-aminobenzoate, and lipoic acid 50 µg; $B_6$ 100 µg. One gram of yeast extract was sometimes substituted for tryptophan. ANS plating medium is made anaerobically with 1.8% Bacto agar and ANS defined medium. Aspartic acid (50 mg/l) is added to the plating medium. ANS/CSL medium contained NaCl 1.0, $K_2HPO_4$ 3.0, $MgCl_2$-$6H_2O$ 0.2, CaCl $2H_2O$ 0.4, $(NH_4)_2SO_4$ 1.0 g/l and corn steep liquor (CSL) 20.0 g dw per liter (Corn Products Corporation). The YE/PEP medium was made with Bacto yeast extract 5.0 g and peptone 10.0 g/l substituted for the CSL in ANS/CSL medium.
Selective Isolation:

Plates containing ANS defined medium and fluoroacetate (5–10 g/l) were suffused with cells of *A. succiniciproducens* grown in same medium by spreading 0.1 ml from a 18 hour old culture. Plates were incubated in an Oxoid jar (Oxoid Ltd., Basingstoke, England) for 18 to 24 hours. Well isolated colonies of resistant cells were picked and washed into vials of ANS/CSL medium with 23 G needles. Vials were incubated for 24 hours and were determined for acetic acid by HPLC. Cells from vials with markedly reduced acetic acid were plated and colonies were reisolated from plates containing the same or higher concentrations of fluoroacetate.
Chemicals:

Sodium monofluoroacetate was obtained from Sigma Chemical Co. (Saint Louis, Mo.).
Analysis:

The organic acid fermentation products were determined using high-performance liquid chromatography (HPLC) (2). Components were analyzed chromatographically by elution with 0.006N $H_2SO_4$ from a cation exchange resin in the hydrogen form. A waters Model 600 HPLC system with a Bio-Rad HPX-87H column and a Waters Model 410 Refractive Index detector were used in this analysis. Carbohydrate was also determined by HPLC.
Serum Vial Cultures:

Serum vial culture technique was used and all transfers were made by syringe. $MGCO_3$, 20 g/l, was added to the vials for pH maintenance. All vials were incubated at 37° C. in a model G25 Incubator Shaker (New Brunswick Scientific, Edison, N.J.).
Fermentation:

One liter batch fermentations were conducted in 2-liter MultiGen fermenters (New Brunswick Scientific, Edison, N.J.). The temperature was controlled at 39° C. Carbon dioxide was sparged at 0.05–0.1 volume/volume/minute. The culture was stirred at 300 rpm with flat blade turbine impellers. The pH was automatically controlled (Chemcadet, Cole Palmer, Chicago, Ill.) at 6.2 with the addition of 1 N NaOH and 1.5M $Na_2CO_3$ or combinations of NaOH and $Na_2CO_3$.
Results A defined medium suitable for the growth of *A. succiniciproducens* and containing fluoroacetate was used to select isolates of *A. succiniciproducens* resistant to fluoroacetate. The variants were selected without the use of any mutagenic technique to avoid obtaining strains with undesirable secondary mutations. Most of the resistant isolates produced very little acetic acid from dextrose. The variant FA-10 was typical of these isolates and the general growth characteristics of FA-10 and the parent strain were the same in 10 ml serum vials. The vial culture products of FA-10 are given in Table 1, along with the products produced by its parent. The same amount of succinate was produced by both strains, but the rest of the product profile was markedly different. FA-10 produced very little acetic acid in contrast to the parent which produced 3.1 g/l. FA-10 accumulated 3.4 grams of the pyruvic acid. The FA-10 variant was stable and maintained its acetate minus character through repeated subcultures.

TABLE 1

Products in serum vial cultures 10 ml of ANS/CSL medium.

| | Succinic (g/L) | Acetic (g/L) | Formic (g/L) | Pyruvic (g/L) |
|---|---|---|---|---|
| A. succiniciproducens | 14.4 | 3.1 | 0.4 | 0.0 |
| FA-10 | 14.6 | 0.1 | 0.0 | 3.4 |

In a fermenter using the same medium with additional dextrose, FA-10 produced 34.1 grams of succinic acid along with very little acetic acid (Table 2). Pyruvic acid also accumulated, 15.6 grams remained when the fermentation was terminated. Pyruvic acid is not a typical end-product of fermentation but is a metabolic intermediate. Pyruvic acid occasionally accumulates in parent A. succiniciproducens fermentations and is completely reassimilated and utilized during the normal course of the fermentation is complete. The remaining carbon in pyruvic acid may be recovered through the optimization of fermentation conditions that favors its assimilation and utilization. In this FA-10 fermentation there is partial utilization of pyruvate between 30 and 44.5 hours.

TABLE 2

Acids (g/l) produced by FA-10 in a 1-liter fermentation.

| Time (hr.) | Dextrose | Succinic | Acetic | Formic | Pyruvic |
|---|---|---|---|---|---|
| 0.0 | 52.1 | 0.4 | 0.0 | 0.1 | 0.8 |
| 18.5 | 21.9 | 20.1 | 0.3 | 0.3 | 12.2 |
| 30.0 | 3.6 | 31.5 | 0.6 | 0.6 | 17.2 |
| 44.5 | 0.3 | 34.1 | 0.4 | 0.4 | 15.6 |

ANS/(2%)CSL medium

For comparison, Table 3 gives the results of a fermentation by the parent strain. In this fermentation yeast extract and peptone replaces CSL.

TABLE 3

Acids (g/l) produced by A. succiniciproducens in a 1-liter fermentation.

| Time (hr.) | Dextrose | Succinic | Acetic | Formic | Pyruvic |
|---|---|---|---|---|---|
| 0.0 | 48.7 | 0.2 | 0.1 | 0.0 | 0.0 |
| 6.0 | 44.3 | 4.5 | 1.3 | 0.4 | 0.0 |
| 15.3 | 18.0 | 22.0 | 5.8 | 0.8 | 0.0 |
| 23.5 | 9.8 | 26.8 | 7.0 | 0.8 | 0.0 |
| 30.5 | 5.9 | 29.9 | 7.7 | 0.8 | 0.0 |
| 40.3 | 3.4 | 31.6 | 8.3 | 0.8 | 0.0 |

YE/PEP medium

It will be apparent to those skilled in the art that a number of modifications and changes can be made without departing from the spirit of the invention. Therefore, it is intended that the invention only be limited by the claims.

References

1. Baronofsky J. J., W. J. A Schreurs, and E. R. Kashket. (1984) Uncoupling by acetic acid limits growth and acetogenesis by *Clostridium thermoaceticum*. Appl. Environ. Microbiol. 48:1134–1139.

2. Guerrant et al. (1982). J. Clinical, Microbiol., 16:355.

3. Samuelov, N. S. et al (1991) Influence of $Co^2$-$HCo^{3-}$ Levels and pH on growth, succinate production, and enzyme activities of *Anaerobiospirillum succiniciproducens*. Appl. Environ. Microbiol. 57:3013–3019.

4. Rothstein, D. M., (1986). *Clostridium thermosaccharolyticum* strain deficient in acetate production. J. Bacteriol. 165: 319–320.

We claim:

1. In a method of producing succinic acid by the fermentation of a carbohydrate containing medium with *Anaerobiospirillum succiniciproducens*, said improvement comprising employing as the *Anaerobiospirillum succiniciproducens* a variant of parent strain *Anaerobiospirillum succiniciproducens* ATCC 29305 which will grow in a medium containing 5 g/l to 15 g/l of sodium monofluoroacetate and which produces less acetic acid and more succinic acid under identical conditions than the parent *Anaerobiospirillum succiniciproducens* of which it is a variant.

2. The method of claim 1 in which the variant is FA10 (ATCC No. 55617).

3. In the method of preparing succinic acid by the fermentation of a nutrient medium containing fermentable carbon with *Anaerobiospirillum succiniciproducens*, the improvement which comprises employing as the *Anaerobiospirillum succiniciproducens* a variant of *Anaerobiospirillum succiniciproducens* ATCC No. 29305 which will grow in medium containing about 5 g/l to about 15 g/l concentrations of sodium monofluoroacetate, said variant having all of the identifying characteristics of FA10 (ATCC No. 55617).

4. A method for the production of succinic acid which comprises providing an aqueous fermentation medium containing a culture of a microorganism and a source of assimilable carbon and cultivating said microorganism under anaerobic conditions in the presence of carbon dioxide to form succinic acid in a concentration of at least about 25 g/l in said fermentation medium; wherein said microorganism is a variant of parent strain *A. succiniciproducens* ATCC No. 29305, said variant being able to grow in medium containing concentrations of about 5 g/l to about 15 g/l of sodium monofluoroacetate, and to produce more succinic acid and less acetic acid than the parent strain under otherwise identical conditions.

5. The method of claim 4 in which the variant is FA10 (ATCC No. 55617).

* * * * *